(12) United States Patent
Coates

(10) Patent No.: US 11,237,140 B2
(45) Date of Patent: *Feb. 1, 2022

(54) MULTI-COMPONENT GAS AND VAPOR MONITORING SENSOR

(71) Applicant: SAAM, INC., Indianapolis, IN (US)

(72) Inventor: John Coates, Newtown, CT (US)

(73) Assignee: SAAM, INC., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/881,674

(22) Filed: May 22, 2020

(65) Prior Publication Data
US 2020/0284774 A1 Sep. 10, 2020

Related U.S. Application Data

(63) Continuation of application No. 16/287,480, filed on Feb. 27, 2019, now Pat. No. 10,663,441, which is a continuation of application No. 15/360,274, filed on Nov. 23, 2016, now Pat. No. 10,241,095.

(60) Provisional application No. 62/258,675, filed on Nov. 23, 2015.

(51) Int. Cl.
*G01N 33/00* (2006.01)
*G01N 21/3504* (2014.01)

(52) U.S. Cl.
CPC ..... *G01N 33/0027* (2013.01); *G01N 21/3504* (2013.01)

(58) Field of Classification Search
CPC .... G01N 21/31; G01N 21/3504; G01N 33/00; G01N 33/0027; G01N 2201/061; G01J 3/02; G01J 3/50
See application file for complete search history.

(56) References Cited

U.S. PATENT DOCUMENTS

| 7,339,657 B2 | 3/2008 | Coates et al. |
| 2007/0084990 A1* | 4/2007 | Coates ................. G01J 3/0272 250/226 |
| 2014/0226149 A1 | 8/2014 | Coates et al. |

* cited by examiner

*Primary Examiner* — Jamil Ahmed
(74) *Attorney, Agent, or Firm* — Ohlandt, Greeley, Ruggiero & Perle, L.L.P.

(57) ABSTRACT

A series of optical spectral sensors for gas and vapor measurements using a combination of solid-state light sources (LED or Broadband) and multi-element detectors, housed within an integrated package that includes the interfacing optics and acquisition and processing electronics. The sensor is designed to be produced at a low cost and capable of being fabricated for mass production. Spectral selectivity is provided by a custom detector eliminating the need for expensive spectral selection components. The multi-component gas monitor system of the present invention has no moving parts and the gas sample flows through a measurement chamber where it interacts with a light beam created from the light source, such as a MEMS broad band IR source or a matrix of LEDs. A custom detector(s) is/are configured with multi-wavelength detection to detect and measure the light beam as it passes through the sample within the measurement chamber.

20 Claims, 10 Drawing Sheets

| Wavelength (microns) | | | | | | | | | |
|---|---|---|---|---|---|---|---|---|---|
| Filters | CWL | WL1 | WL2 | Est. BP | Filters | CWL | WL1 | WL2 | Est. BP |
| C1 | 8.00 | 7.84 | 8.16 | 0.208 | | | | | |
| C2 | 12.06 | 11.63 | 12.50 | 0.567 | | | | | |
| C3 | 9.44 | 9.26 | 9.62 | 0.231 | C3 | 7.26 | 7.20 | 7.30 | 0.10 |
| C4 | 10.27 | 9.90 | 10.64 | 0.479 | | | | | |
| iC4 | 8.51 | 8.33 | 8.70 | 0.236 | | | | | |
| C5 | 10.90 | 10.80 | 11.25 | 0.293 | | | | | |
| C6 | 11.25 | 11.1 | 11.4 | 0.195 | | | | | |

Fig. 2B

MULTI-COMPONENT GAS AND VAPOR MONITORING SENSOR

CROSS-REFERENCE TO RELATED APPLICATION

This application claims priority from U.S. application Ser. No. 16/287,480, filed Feb. 27, 2019, which claims priority from application Ser. No. 15/360,274 filed Nov. 23, 2016, which claims priority from application 62/258,675 filed Nov. 23, 2015, the disclosures of which are all incorporated herein by reference in their entireties.

FIELD OF THE INVENTION

This invention relates generally to optical sensors, spectroscopy, and associated systems. More particularly, it relates to optical sensors and systems that may be used, for example, for the analysis and characterization of vapors and gases.

BACKGROUND

The analytical spectral region for measurement of gases, vapors, and volatile materials relevant—for example only— to oil, gas, and other applications extends from the ultraviolet (UV) to the mid infrared (mid-IR) spectral regions. Because of this, many applications rely upon infrared gas analyzers that are used for continuously measuring the real-time concentration of each component in a gas sample that contains various gas components by selectively detecting the amounts of infrared radiation absorbed by the gas components. Infrared gas analyzers are widely used in various fields because of their excellent selectivity and high measuring sensitivity.

Non-dispersive infrared (NDIR) techniques for the analysis of gases for individual species monitoring is one common technique used for an infrared gas analyzer. Traditional NDIR instruments primarily involve mechanical elements, such as filter wheels that are used in the selection of specific filters and their location relative to the optical path between the light source, the sample, and the detector. These commercially available systems are classified as instruments or analyzers.

Single-beam and two-beam (double beam) NDIR gas analyzers are available. With single-beam devices, the infrared radiation generated by the infrared emitter is routed after modulation, such as by a rotating diaphragm wheel, through the measuring vessel containing the gas mixture with the measuring gas component to the detector device. In one example configuration for two-beam devices, the infrared radiation may be subdivided into a modulated measuring radiation passing through the measuring vessel and into an inversely-phased modulated comparison radiation passing through a comparison vessel filled with a comparison gas. In such examples, optopneumatic detectors filled with the gas components to be verified and comprising one or more receiver chambers arranged adjacent or to the rear of one another are usually used for the detector device. Such an approach is sometime referred to as infrared gas filter correlation spectroscopy.

Other traditional methods of for analysis of multi-component gas and vapor monitoring include the use of Fourier transform infrared (FTIR) spectroscopy and gas chromatography (GC). FTIR spectroscopy relies heavily on measuring the spectra of the key components and then relying on spectral resolution or mathematics to separate and measure the individual contributions from the components. Gas chromatography physically separates the components by the chromatograph and the separated components are measured directly from the chromatogram by a suitable detection system; such as a flame ionization detection (FID) system. While both of these are standard reference methods, they are both expensive and may generate a significant service or operating overhead when implemented in a continuous monitoring system, particularly in the case of GC, which requires the use of high purity compressed gases. Similarly, mass spectrometry is another method for analyzing multi-component gas and/or vapor analysis that works by measuring the mass-to-charge ratio and abundance of gas-phase ions within a high vacuum. This method is also costly and hard to reduce to a scalable sensor that can be used for commercial sensing aspects.

Other spectroscopy methods used in monitoring fluids include those disclosed in U.S. Pat. No. 7,339,657 to Coates et al., which is incorporated herein by reference. These examples feature near infrared light-emitting diodes (LEDs) are used for oil condition measurements (soot level) and urea. The soot measurement is a simple photometric measurement with one primary wavelength (940 nm), while the urea quality sensor is a true spectral measurement with a three-point determination having two analytical wavelengths, 970 nm and 1050 nm, for water and urea, and one as reference/baseline, 810 nm. In both cases attenuation of signal intensity is used to compute the infrared (near-infrared) absorption, and this is correlated to the concentrations of soot (in oil) and the relative concentrations of water and urea in the binary mixture/solution.

LED components are available that support an extended spectral region from the UV region to around 250 nm and mid-IR from the about 3 to about 5 micron region. These devices are currently expensive, and do not have a good usable lifetime in the context of low-cost automotive sensors. Both of these LED regions are important for the application to gas and vapor sensing. The mid-infrared is an established region for gas and vapor monitoring, primarily the combustion gases, CO and $CO_2$, and to some extent NOx and other pollutant gases. However, some other NOx gases and other vapors have a spectral range in the UV region that these LEDs cannot adequately reach.

However, existing LED sensing platforms are not reliable for high temperature gas monitoring, and the implementation relative to the optics required is difficult, if not impossible. While using a NDIR concept as a dedicated sensor is feasible, it is not practical because a long physical optical path is required for IR detection, and major combustion gas components, such as carbon dioxide ($CO_2$), carbon monoxide (CO) and water, are all infrared absorbers. Water in particular can become a matrix interferent and prevent accurate readings.

Additionally, commercial artificial noses may be used to determine the components of a gas or vapor sample. These artificial noses are based on the responses of an array of conductive polymers that are correlated to smells and odors of gases and vapors. These are expensive devices, are easily contaminated, and are inferential relative to the smell or odor of the vapor. Unlike the spectral nose function of the present invention, these artificial noses have no direct correlation to the actual function of the human nose.

There exists a need to provide the same functionality of the instruments and analyzers described above but within a single electronic package, where the source, sample, and detector are reduced into the size of a sensor package. Additionally, there is a need to provide a sensor that is capable of monitoring a wide spectral band from the UV to the mid-infrared regions. The present invention can be used in a wide variety of industries where gas sensing and monitoring is critical, especially related to the analysis, safety, and measurement of gases and vapors. The present invention also provides a much broader spectral sensor package for vapors, gases, and other materials that were not previously capable of being monitored in a cost efficient manner.

BRIEF SUMMARY OF THE INVENTION

In one aspect, this disclosure is related to a multicomponent gas sample monitoring system comprising a measurement chamber that is configured to allow a gas sample to flow through said measurement chamber, a light beam that interacts with said sample as it passes through the measurement chamber, and a dedicated detector configured to have multi-wavelength detection that is communicatively coupled to a microprocessor.

In another aspect, this disclosure is related to an optical spectral sensing device, for determining properties of a gas sample, where the device comprises a measurement chamber configured to allow a sample pass through the chamber, a light source, a detector system having at least one detector, a coupling apparatus for coupling the light source and the detector system to the measurement chamber, and integrated electronics for providing energy for the light source and for receiving a signal generated by the detector system in response to energy coupled to the detector system by the coupling apparatus. The integrated electronics provide direct output of the properties or composition of the sample. The device can further include a microprocessor communicatively coupled to the device, wherein the microprocessor is configured to calculate, based on the detected gas components, values of the concentrations of the components in the sample of the gas, vapor, or combination of both.

In another aspect, this disclosure is related to an optical spectral sensing device, for determining properties of a gas sample within an enclosure or a large pipe, where the device comprises a measurement chamber configured within an insertion probe where the device comprises an adjustable measurement chamber configured to allow a sample to enter through the walls of the insertion tip into the measurement chamber, a light source, a detector system having at least one detector, an integrated optical coupling the light source and the detector system to the measurement chamber, and integrated electronics for providing energy for the light source and for receiving a signal generated by the detector system in response to energy coupled to the detector system by the coupling apparatus. The integrated electronics provide direct output of the properties or composition of the sample. The device can further include a microprocessor communicatively coupled to the device, wherein the microprocessor is configured to calculate, based on the detected gas components, values of the concentrations of the gas or vapor components in the sample.

In yet another aspect, this disclosure relates to an ambient air sensor for determining the composition of a gas sample, where the device comprises a measurement chamber configured to allow a sample pass through the chamber, a light source, a detector system having at least one detector, a coupling apparatus for coupling the light source and the detector system to the measurement chamber, an extractor configured to draw the sample into the measurement chamber, and integrated electronics for providing energy for the light source and for receiving a signal generated by the detector system in response to energy coupled to the detector system by the coupling apparatus. The integrated electronics provide direct output of the properties or composition of the sample. The device can further include a microprocessor communicatively coupled to the device, wherein the microprocessor is configured to calculate, based on the detected gas components, values of the concentrations of the gas or vapor components in the sample.

In yet another aspect, sensing systems based on a multiplicity of wavelengths, where the wavelengths are statistically selected to determine chemical or molecular functionality. In this configuration the sensing system includes computational methods that provide a matching to functionality, including pattern recognition or artificial intelligence methods, where material identification, composition, or both are provided as an output. The infrared spectrum provides a signature based on molecular vibration. The unique vibrations of a functional group provide a characteristic signal that can be used to identify substances. In this mode the sensor function similar to that of a nose, artificial or human.

Another aspect of the present invention is a method for identifying the component gases and vapors of a sample, comprising statistically selecting at least one specific wavelength to determine a components chemical functionality. Detecting a first specific wavelength intensity of multi-wavelength radiation transmitted through the sample by a first wavelength specific detector. Detecting a second specific wavelength intensity of multi-wavelength radiation transmitted through the sample by a second wavelength specific detector. Detecting a third specific wavelength intensity of multi-wavelength radiation transmitted through the sample by a third wavelength specific detector. Detecting a fourth specific wavelength intensity of multi-wavelength radiation transmitted through the sample by a fourth wavelength specific detector. Determining a presence of a component gas or vapor in the sample based at least in part on the detected first, second, third and fourth intensities. This approach can be fabricated to include a multiplicity of wavelengths beyond four and can be configured for as many as 24 sets of gas detection elements based on wavelength and intensity.

BRIEF DESCRIPTION OF THE DRAWINGS

The features and advantages of this disclosure, and the manner of attaining them, will be more apparent and better understood by reference to the following descriptions of the disclosed system and process, taken in conjunction with the accompanying drawings, wherein:

FIG. 2B is a chart of example infrared bandpass filters selected for the detection and measurement of specific hydrocarbons in the gas or vapor phase.

DETAILED DESCRIPTION OF THE INVENTION

Figure 1A:
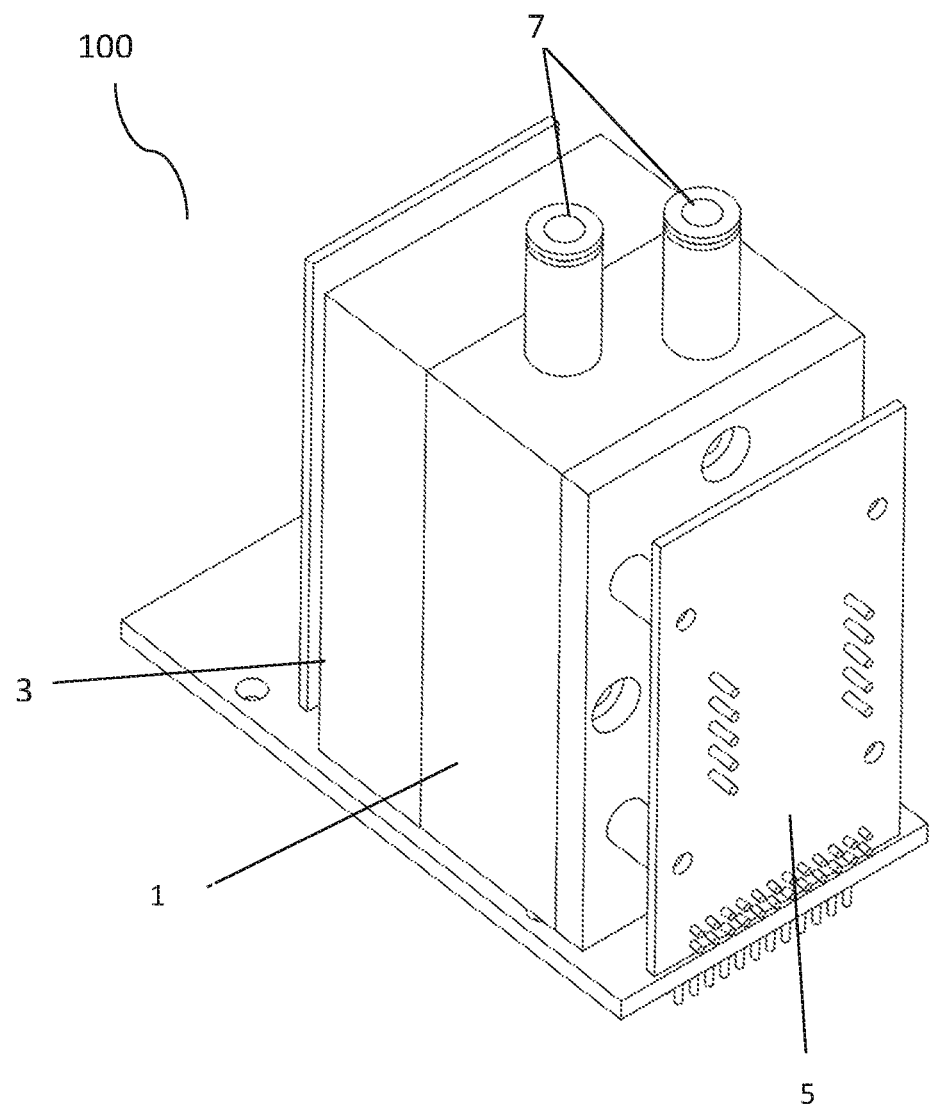
FIG. 1A is a perspective view of an exemplary embodiment of the multi-component gas monitor system, quad detector, and example bandpass filter sets.
Figure 1B:
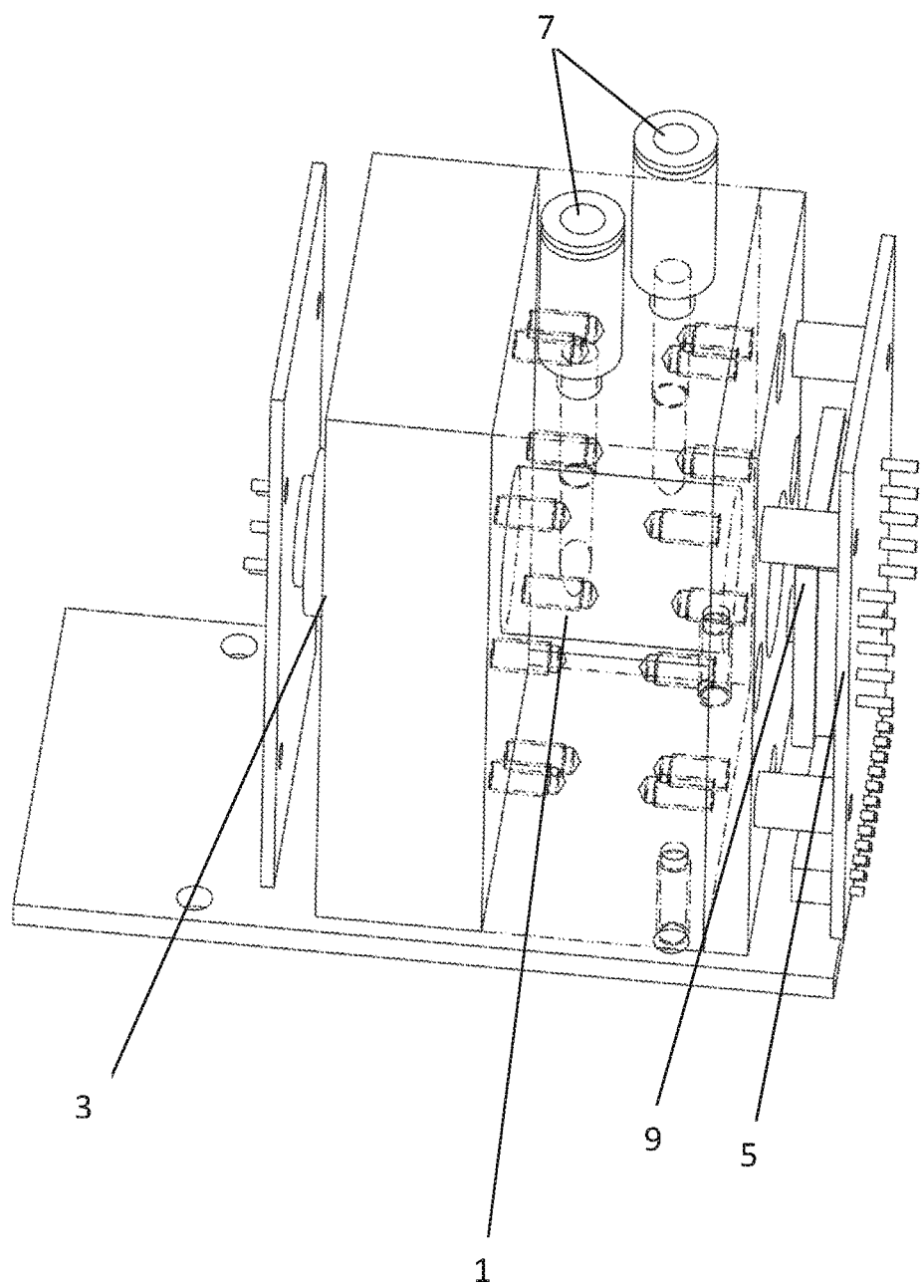
FIG. 1B is a perspective view of an exemplary embodiment of the multi-component gas monitor system, quad detector, and example bandpass filter sets with a portion of the system being transparent.

An exemplary embodiment of the present invention provides the same functionality that exists in current gas system analyzers and spectrometers but within a single electronic package, where the source, sample and detector can be reduced in size to be used as a low cost sensor for multiple applications. As shown in FIGS. 1A-B, the multi-component gas monitor system 100 of the present invention can have no moving parts and the gas sample flows through a gas sensing/measurement chamber 1 where it interacts with a light beam created from a broadband emitter 3, such as a tungsten light source, a solid-state device such as a micro-electromechanical system (MEMS) infrared emitter, or a composite or enhanced LED array light source. One preferred embodiment of the multi-component gas monitor system uses a MEMS infrared emitter for the mid-infrared sensors. A dedicated detector system 5, which is configured with multi-wavelength detection, can detect the light beam as it passes through the sample within a measurement chamber. These measurement chambers can be customized and optimized for specific applications. The system can have ports 7 that are fluidly connected to the sample chamber to allow for the flow of a gas through the sample chamber.

One exemplary embodiment can have a straight-through profile with the internal optical path set to between about 1 mm and about 100 mm. The path length is optimized for the species being measured and the anticipated concentrations. Similarly, the minimum chamber volumes that result from this geometry can range from less than about 1 mL up to about 50 mL, depending upon the path length and the number of channels that will be monitored. This provides for a more compact sensor than other current applications.

Figure 1C:
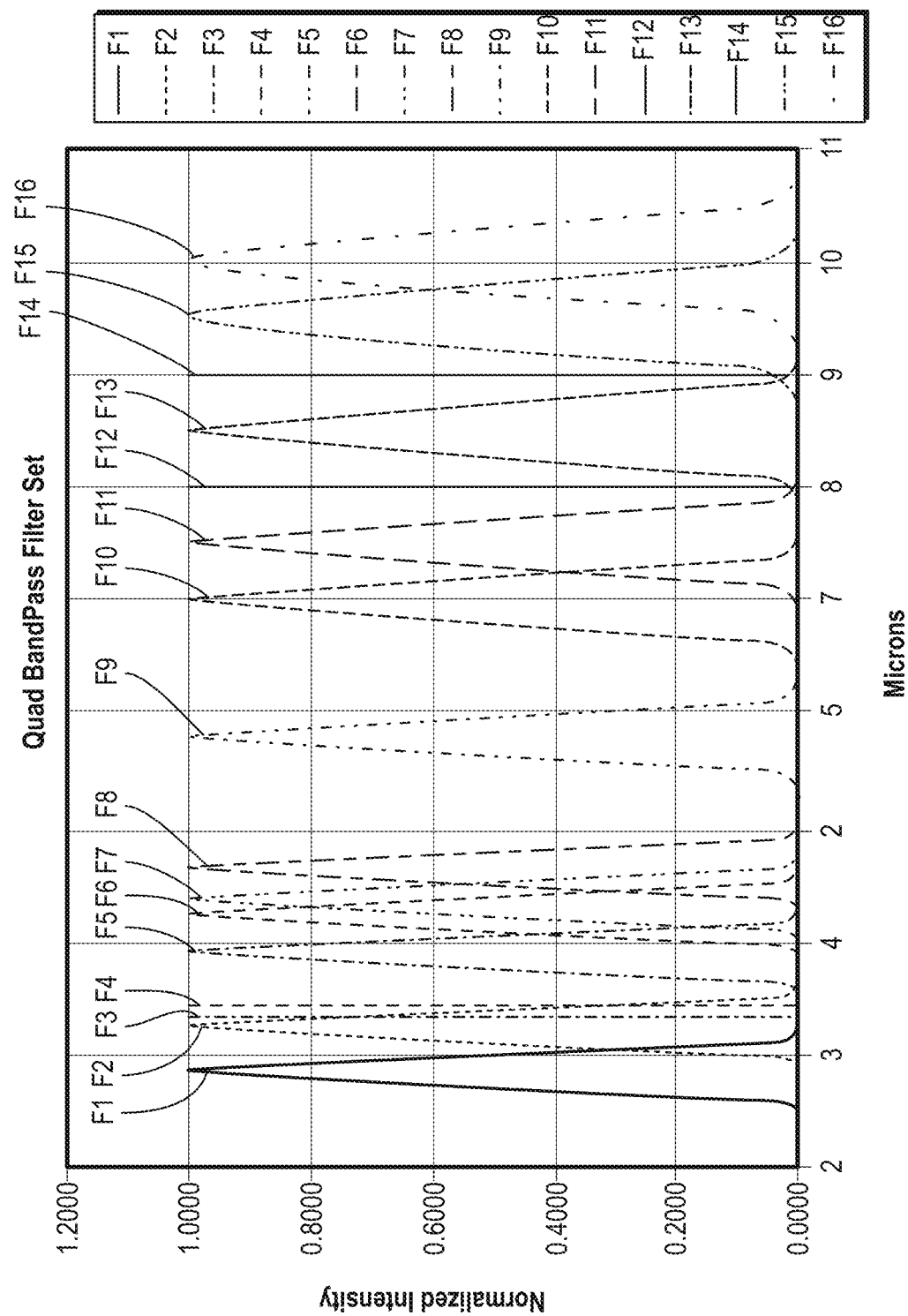
FIG. 1C is a chart of exemplary filter profiles that may be selected and used for detector customization.

A single dedicated detector component 7 can combine up to four specific wavelength filters that are selected to measure specific chemical compounds, allowing for multi-wavelength detection in a single package. Detectors can be fabricated for standard gases, in particular the carbon oxides (CO and $CO_2$), ammonia and hydrocarbons. When evaluating the full infrared spectrum, a user can select filters that can provide specific detection for virtually any chemical compound in gas or vapor form. FIG. 1C provides a chart for example filter profiles that may be selected and used for detector customization. Combining one or more of these custom detectors can be applied to a range of spectroscopic applications, especially when used with spectroscopic software to perform complex analyses for multicomponent chemical systems.

The present invention can be utilized as a compact low cost analyzer for use in the automotive industry, the energy industry, and any industry in general to monitor, for example, natural gas for its composition. Another use for the present invention is in consumer sensors for gas sensing within a consumer's home or workplace. These can be considered 4- or 8-channel applications, where the three basic fuel gases, i.e. methane, ethane and propane, can be measured with a 4-channel device, and a full hydrocarbon profile, e.g., methane to hexane, can be monitored on an 8-channel device. Such measurements can be used for the assessment of the fuel quality and fuel combustion efficiency. These analyses are traditionally measured by more sophisticated instrumentation, and would not be considered possible by a simple in-line sensor like the multi-component gas monitoring system of the present invention. In another variant for fuel composition sensing a multi-wavelength version can be implemented to differentiate kerosene from diesel fuel.

Another application of the present invention is using the multi-component gas monitoring system for hydrocarbon vapor monitoring for smog related applications where vapors from fuel dispensing systems have to be monitored, as required by the Environmental Protection Agency (EPA) for gas stations. Measurements of benzene-toluene-xylene (BTX) are particularly of importance for smog control applications where real-time monitoring of BTX species can be used to estimate the impact of spills and fugitive emissions from dispensing systems and storage tanks. This application of the present invention is greatly benefited by a hybrid detection system that can utilize both UV and mid-infrared detection.

Similarly, the present invention can also be used in the power generation and distribution sector, where the multi-component gas monitoring system can be used for hydrocarbon vapor monitoring in the headspace of a power transformer. The number one failure mode of a power transformer on the grid is either a fire or an explosion. This is caused by a build-up of highly flammable gases, possibly even at explosive levels, resulting from the degradation of the insulating medium, a highly refined mineral oil. The ingress of moisture over time can result in a breakdown of the insulating properties of the oil, leading to internal arcing that causes degradation to produce highly flammable gases such as acetylene, ethylene and carbon monoxide. The present invention can be configured to detect the formation of these gases providing pre-emptive information that can provide service information leading to the prevention of this failure mode.

Another commercial application of the present invention is use for the detection of alcohol and related compounds for breath measurements for blood alcohol level determinations. Such technology can be used for law enforcement and also onboard interlock devices for the ignition control of a vehicle. The latter can be used for legal or sentencing enforcement related to DUI management. The infrared sensor can be configured to monitor alcohol and differentiate from potential interferences such as acetone (diabetics), methanol (windshield washer fluid) and isopropyl alcohol (rubbing alcohol).

Another application of the present invention is in the medical market sector for the monitoring of anesthesia gases in the operating room. The multi-component gas monitor system can be used in two modes. The first mode is an ambient monitoring mode for the presence of anesthesia gases in the air, patient monitoring for the delivery of anesthesia gases during an operation, or the release of anesthesia gases during post-operative recovery. A second configuration of the sensor can be optimized for ultra-low volume detection matched to the gas volumes applied to patients, including infants in a neonatal setting or to animals in a veterinary setting.

The present invention provides these measurements from a simple sensor based on the use of spectroscopic multi-component tools, and smart sensing methods. Other spectral regions can be analyzed, including the UV, near infrared, and in the case of the present invention the infrared. In some cases a mix of detection modes may be used in the form of a multi-wavelength hybrid detector. The device can receive low-level power, which can be provided by a data bus or via a normal power distribution system of a vehicle or a mobile system running from batteries. The output from the sensor, in some form of data communications, can be fed back to a display, a data bus, or an on-board computer system. FIGS. 1A-B illustrates a simple sensor by showing a simple 4-channel system for natural gas analysis, the electronic component containing the detector system, and example wavelengths that are available based on available filters (FIG. 1C).

These filters are integrated into the custom detector system 5 for the multicomponent gas sensors by dicing the filters into small fragments and then mounting them above the individual detector elements. FIG. 2B defines the filter's wavelengths capable of making this analysis. This application differs from normal filter photometers insofar as a standard filter photometer requires that the sample gas absorption is isolated from other absorptions of other gas components. The present invention is configured to handle the spectral overlap of various gases through multicomponent computational methods used for the data handling of the sensor. A multivariate model is built up from the spectral responses at the filter wavelengths shown in FIG. 2B, based on the detection of the component gases or vapors.

Conducting measurements that require more than four channels may require an 8-channel measurement system. Each component gas requires at least one wavelength to represent that component. Combining two of the 4-channel detectors with suitable electronics can provide a measurement system for full component analysis of natural gas. This example system provides real-time output for up to 8 of the component gases simultaneously at about a 10 Hz modulation rate (4 KHz data rate). FIG. 1A-B illustrates exemplary embodiments of the present invention for various gas measurements, including natural gas monitoring. The architecture of these embodiments can have path lengths ranging from about 1 mm to about 100 mm or more. Some exemplary embodiments of the present invention are based on about a 10 mm to about 20 mm physical optical path length, which is optimized for gas mixtures containing higher concentrations of methane, and lower concentrations of butane, ethane and propane.

By limiting the measurement to the 4-channel system with the gas measurement filters being selected with wavelengths less than about 5.0 microns, all of the target gases used for natural gas quality measurements can be precisely captured within a single measurement package with a defined path length of about 10 mm to about 20 mm. Extending this path length can increase measurement sensitivity. A further benefit of the 4-channel spectral region is that low cost optics and materials of construction may be used. One exemplary embodiment can use a small diameter quartz or sapphire window, with a simple metal construction used for the measurement chamber and o-ring compression seals.

Figure 2A:
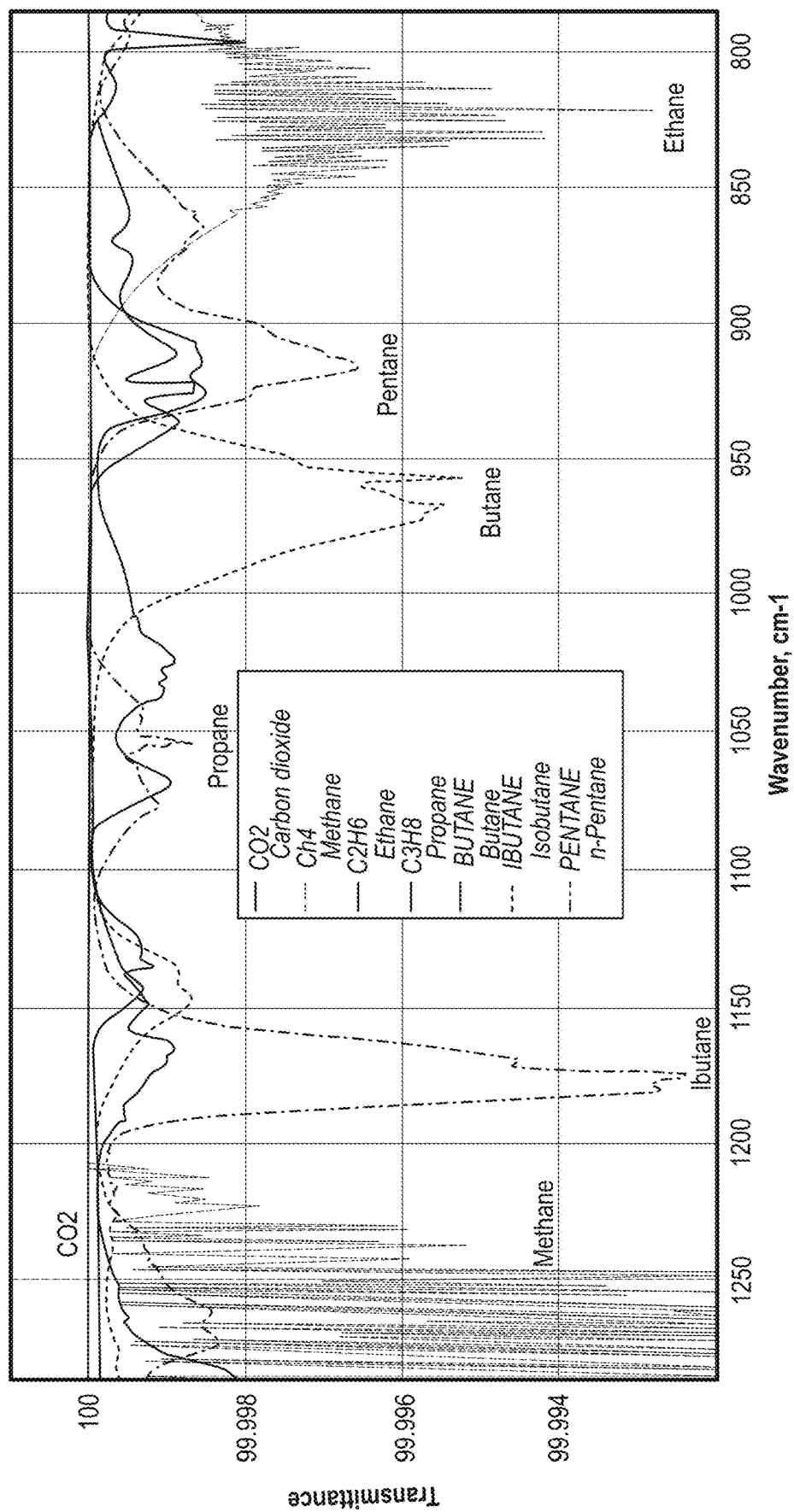
FIG. 2A is a graph of an infrared gas phase spectra of simple aliphatic hydrocarbons.
Figure 3:
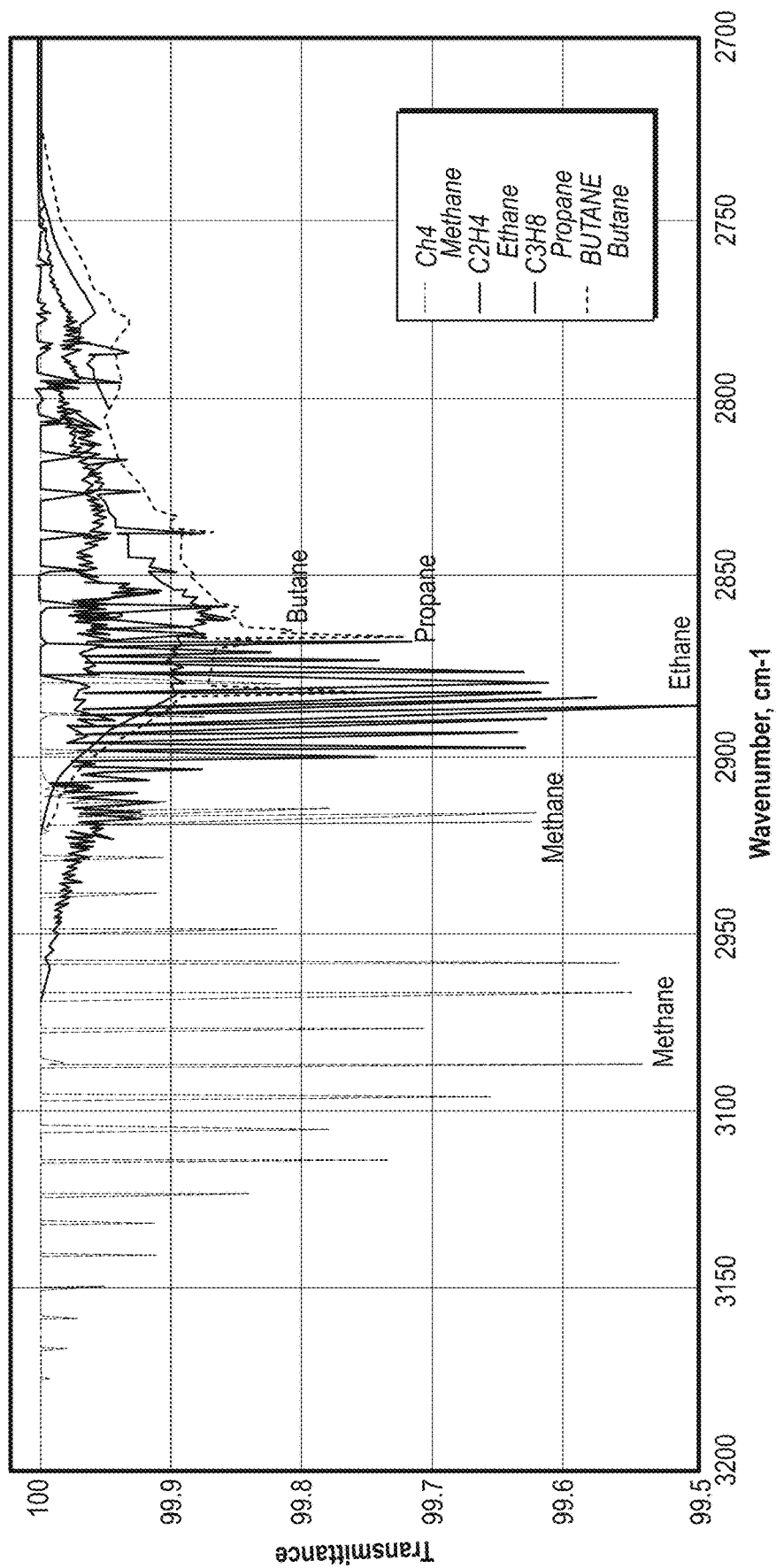
FIG. 3 is a graph of infrared gas spectra of natural gas hydrocarbons, C1 to C4

The 4-channel sensor can have a primary spectral region defined as the C—H stretching or vibration region. This region provides absorptions that have high absorptivities and provide good measurement sensitivities. By extending the wavelength range to include the more fundamental vibrations and the C—H bending vibrations, clearer band separation can be achieved, but at the cost of reduced absorptivity and measurement sensitivity. FIGS. 2A and 2B indicate the use of these optional longer wavelengths, and these are enabled by the use of extended optical/physical path lengths.

A second configuration of the present invention can have an optimal wavelength range from about 5.5 microns to about 12 microns. In this spectral range it is possible to separate the gas species from C1 to C6 using the wavelengths defined in FIG. 2B. The actual spectra for C1 to C5, including i-C4 (isobutane) are provided in FIG. 2A. While some overlap exists between C5 and C6, each species may be differentiated by careful selection of the measurement range using filters with center wavelengths of about 10.9 and about 11.25 microns. This secondary wavelength range can be accommodated with an optical path length of about 50 mm to about 100 mm. These longer path lengths are better suited for low level (e.g., parts-per-million (ppm)) detection of gases.

This configuration is particularly useful for natural gas measurements, with the normal composition of C1 to C5, with the capability of being extended to C6. Because the higher molecular weight compounds, C5 and C6, are liquids at room temperature, it is necessary to elevate the measurement temperature to about 40° C. or to about 50° C. At normal ambient temperatures of about 20° C. to about 25° C. there is a risk of condensation of these materials, which can lead to errors in measurement due to the loss of the C5/C6 to the walls of tubing or tanks and the condensate possibly dissolving some of the light hydrocarbon gases.

Referring to FIGS. 1A-B, a measurement system with a path length of about 50 mm and 8-channels is capable of being operated at temperatures up to and possibly greater than about 120° C., thereby making them suitable for natural gas measurements over the full range of natural gas compositions. This includes compositions with hydrocarbons up to C6 or higher.

The analytical performance of the sensors illustrated in FIGS. 1A-B are defined by the multi-channel, multi-wavelength detectors that are used. The type of detector and the use of the detector are important in terms of gaining the optimum performance and sensitivity from this class of detector. In the mid-infrared spectral region there are typically two classes of detectors, which are thermal and photo detectors. Most low cost detectors are adaptations of the thermal detectors, and typically either thermopile/thermocouple detectors or pyroelectric detectors. Thermopile/thermocouple detectors are slow in response and are best used in a continuous wave or DC mode where the output of the detector is measured when energy falls on the detector and comparing this output to when the energy is switched off. The output may be modulated to differentiate from ambient thermal radiation, but may also work with low modulation rates.

One preferred embodiment of the present invention can use pyroelectric detectors, which can be modulated at higher frequencies. The pyroelectric detector has a sinusoidal style of response function and the required electronics must provide synchronization of the waveform with the pulsing of the light source. The electronics can feature on-board microprocessors that can operate with customized firmware, providing on-board data processing options, as well as customized data output formats and electronic interfaces. These electronics can be optimized for an onboard microprocessor by providing data acquisition rates as high as about 1 KHz per sample channel (4 KHz overall for all four channels). Higher rates may be accommodated, possibly with alternative processors, such as a digital signal processor (DSP) or application-specific integrated circuit (ASIC) processors, if additional processing, such as block averaging or digital filtering, is to be used in real-time. The electronic interfaces can support any suitable communication connectors, including USB, serial and CAN data communications formats.

A modulated light source can be used to encode the light passing through the gas sample and to synchronize with the pyroelectric detectors. The detectors can also come in a surface-mount device (SMD) format and provide signal-to-noise ratio (SNR) performance up to about 40,000:1 within a tenth of a second, depending upon the analysis wavelength and the level of signal filtering that must occur. This can provide ppm level of detection and measurement sensitivity for a wide variety of gases and vapors. MEMS based IR sources are typically required for this IR light source modulation. These sources can be designed to be optimally modulated in the range of about 10 Hz to about 20 Hz, but some systems can be modulated as high as about 50 Hz to about 100 Hz. Modulating at this higher range can result in a sacrifice of modulation depth, thereby limiting measurement sensitivity.

The present invention can use multiple 4-channel detectors where each channel is linked to a unique wavelength that is intended for detection of a specific gas or class of gas species or statistically correlated gas or vapor species. One exemplary embodiment of the present invention uses four 4-channel detectors that provides 16-channels for real-time measurement. The four specific wavelength channels are illuminated by a modulated light source and are detected by each of the detector channels, and digitized by a 4-channel analog-to-digital (A/D) converter. The digitized signal from each channel is linked to the detection of multiple gas species intended for detection by the multi-channel gas sensor. This implementation is the basis of an infrared spectral nose.

The infrared spectral nose configuration functions by sensing based on a multiplicity of wavelengths, where the wavelengths are statistically selected to determine chemical or molecular functionality. In this configuration the sensing system includes computational methods that provide a matching to functionality, including pattern recognition or artificial intelligence methods, where material identification, composition, or both are provided as an output. The infrared spectrum provides a signature based on molecular vibration. The unique vibrations of a functional group provide a characteristic signal that can be used to identify substances.

Another application of the present invention, specifically the spectral nose configuration, is in environmental, public safety and fire prevention sector where the multi-component gas monitoring system is used for the ambient air monitoring in rooms, homes, offices, warehouses, storage areas, and other rooms for toxic and flammable gases. In a configuration with multiple channels, such as up to 16-channel system, the system implementations can range from HVAC systems in offices and public places, consumer home monitoring, to warehouses used to store solvents and chemicals. The output of the sensor can be programmed to detect leaks and spills that could lead to fires or explosions and used as pre-emptive fire prevention. Additionally, the sensor can be used to detect the generation of a dangerous environment relative to the presence of toxic or poisonous gas or vapors.

The digital signal from each channel is evaluated relative to one or more reference signals, and the concentration of the gases are calculated from stored calibration equations for each species measured. These computations can be completed onboard the sensor with the onboard microprocessor, or through an external computer or data logging system interfaced with the sensor. DSP microprocessors, such as those with an ARM architecture, or a custom ASIC can be implemented when higher levels of digital sampling (>4 KHz) are required for specific applications. Similarly, higher data rates may be desired if a significant amount of data preprocessing or signal pretreatment is necessary, such as noise reduction or spectral matching or modeling, which can be vector based.

In one standard geometry, an exemplary embodiment of a gas sensing system is a straight through configuration where the light from the source, such as a modulated IR source, passes through the gas within a tubular arrangement as illustrated in FIGS. 1A-B. In this embodiment, the gas is fed into the sensor from couplings/fittings 7 mounted on top of the multi-component gas monitoring system 100 using any suitable components, such as standard gas fittings. The gas may enter and exit from the same side of the sensor or on opposite sides, depending on the application. Gas mixing and reduction of dead regions can be accomplished and varied based on the gas flow rate. The present invention can provide minimal back pressure and can allow consistent rapid data updating and fast sample turn over within the sensor. In the case of the natural gas sensor, the sample interchange is rapid, and even at low flow rates, the small dead volume of a few mL ensures a rapid interchange of the gas samples being measured.

Alternative embodiments of the present invention for high efficiency optical coupling and low sample dead volumes can be include various designs. In one alternative embodiment, a highly efficient sampling interface with minimum dead volumes, where two orthogonal sampling channels were used to reduce the overall system size and can have a sample volume of <1 mL. The inlet pipes can also improve sampling efficiency and remove dead volume. This exemplary embodiment can be used for anesthesia gas monitor, where a high data rate is required with a rapid sample turn-over and interchange. Another exemplary embodiment, can have high optical efficiency, where the image from the source is captured at a focal point of an ellipsoidal mirror and reimaged back on to a detector. The IR radiation passes twice through the gas that is captured between two transmitting windows. The gas can pass side to side and can have a minimum dead volume. The total optical path length in this embodiment can be set to about 50 mm.

Yet another embodiment, the present invention can have a cross-pipe configuration where the gas being measured flows through a pipe and the infrared beam can pass across the flow path of the gas. This embodiment can have an optical path length of about 10 mm to about 20 mm and does not typically have a trapped volume for the gas. Because there are no physical constraints for either the gas flow or the light path, this embodiment is highly efficient.

Figure 4A:
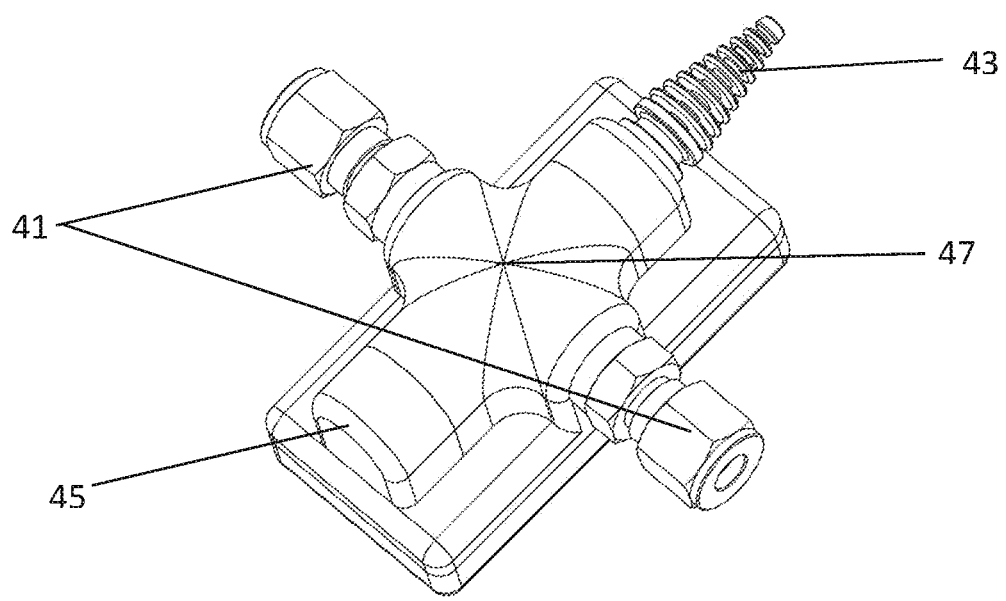
FIG. 4A is a perspective view of an exemplary embodiment of a gas sensor with integrated optics, gas interface and electronics.
Figure 4B:
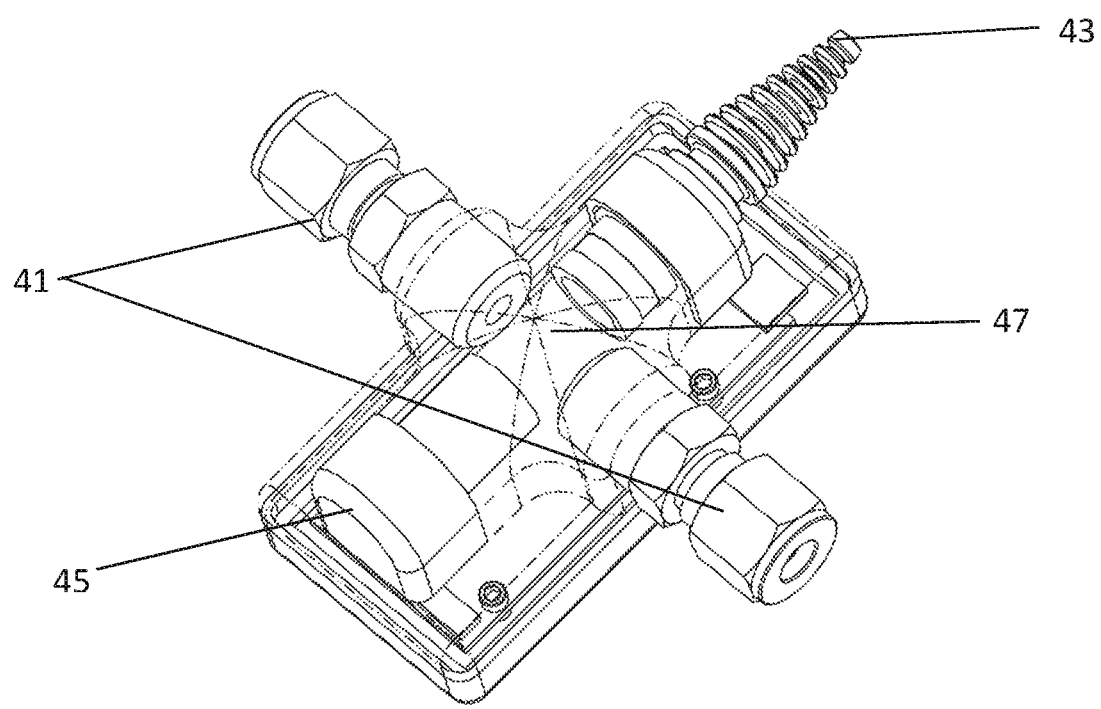
FIG. 4B is a perspective view of an exemplary embodiment of a gas sensor with integrated optics, gas interface and electronics with a portion of the system being transparent.

FIG. 4A-B illustrates a further adaption of cross-pipe embodiment and incorporates measurement electronics. This embodiment can be used as an integrated sensor system for low volume gas sensing in environmental, industrial, commercial and automotive applications. The sensor can use any suitable coupling 41, such as a standard Swagelok®, Circor® or Parker® style compression coupling, which can be attached to an inner chamber 47 and fitted with sealed windows. The sealed windows can use any suitable material, such as quartz, sapphire, barium or calcium fluoride, or Cleartran™. The source 43 and detector 45 can be juxtaposed to optimize optical coupling. Additionally, the electronics can be close-coupled to reduce connector wire lengths and minimize signal pickup. The entire package is optimized for size and optical/pneumatic efficiency for gas measurements.

Figure 5A:
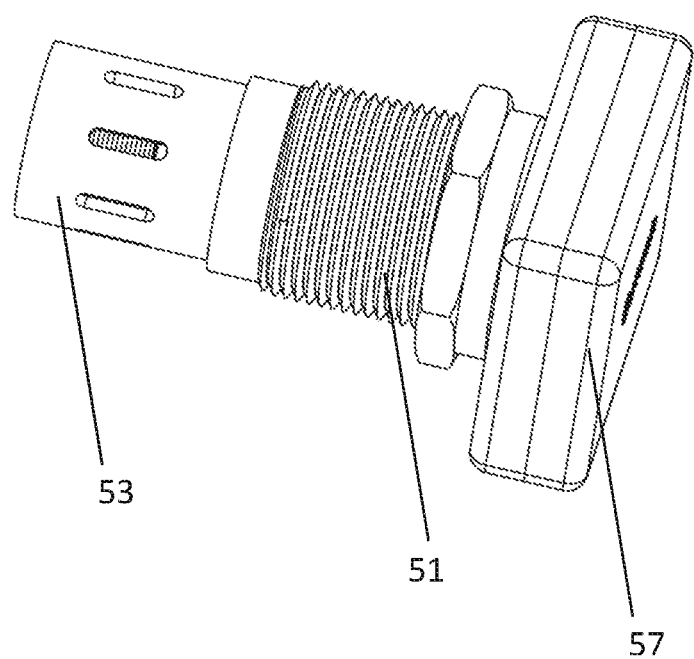
FIG. 5A is a perspective view of an exemplary embodiment of an insertion style gas sensor with integrated optics, gas interface and electronics.
Figure 5B:
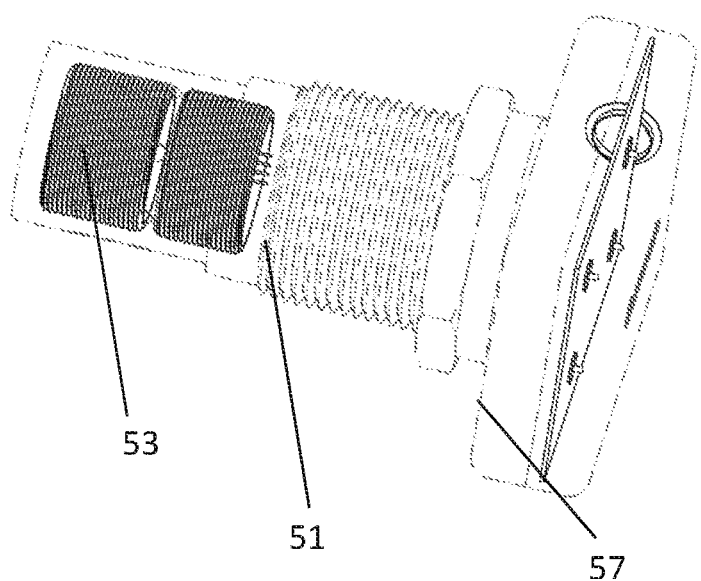
FIG. 5B is a perspective view of an exemplary embodiment of an insertion style gas sensor with integrated optics, gas interface and electronics with a portion of the system being transparent.

The insertion probe, shown in FIG. 5A-B, may also be used in these environments where the probe is placed within an air or gas flow within piping or HVAC conduit. This insertion probe can use a retroreflective head to allow for a remote sampling probe. The insertion probe embodiment can comprise a measurement chamber 51 configured within an insertion probe where the device comprises an adjustable measurement chamber configured to allow a sample enter through the walls 53 of the insertion tip into the measurement chamber, a light source 55, a detector system 57 having at least one detector, an integrated optical coupling the light source and the detector system to the measurement chamber, and integrated electronics for providing energy for the light source and for receiving a signal generated by the detector system in response to energy coupled to the detector system by the coupling apparatus. The integrated electronics provide direct output of the properties or composition of the sample. The device can further include a microprocessor communicatively coupled to the device, wherein the microprocessor is configured to calculate, based on the detected gas components, values of the concentrations of the gas or vapor components in the sample.

The present invention is directed to the use of optical components and elements, such as windows with o-ring seals, without the use of cumbersome imaging components. The aforementioned embodiments of the present invention can primarily be used for flow-through applications, where gas flows into the sensor through a gas coupling and back out of the sensor. These flow-through sensors can be used for measurements within a piped gas system, and depending on their optical path length, can obtain gas component measurements to as little as less than about 10 parts-per-million (ppm).

A gas sample can be taken from the ambient air environment and drawn into a chamber by a simple extractor fan or a gas/vapor circulation pump. While in the chamber, the gas comes into the optical path of a light source and a detector system. Similar to previously described embodiments, this ambient air embodiment can have sixteen independent channels and can use an optical path length of about 50 mm. This can allow for the sensor to be use with sixteen different wavelengths selected for specific material detection or correlated chemical functionality detection in the ambient air. The ambient air sensor can be used in a multiplex mode to detect a various flammable and/or toxic vapors and used to sense build-up of such gases over time. The wavelengths selected can target specific chemical functionalities and using a pattern matching or statistical correlation algorithms the responses can identify the vapors detected. Once identified the sensor can transmit a signal to flag potentially dangerous conditions upon gas/vapor levels reaching a predetermined threshold, such as a documented explosion limit.

The ambient air sensor has low noise electronics combined with a high sensitivity, wavelength-specific detector system. The sensor can have built-in firmware that permits it to monitor in either a continuous or instantaneous manner at data rates as high as about 20 Hz or more. One exemplary embodiment can use about a 10 Hz system and can provide SNR of about 10000:1 per channel. The sensor can be configured to monitor 16 discrete channels, where each channel can be configured to monitor a specific chemical entity or gas component. Additionally, in the multiplex mode the 16 channels can be modeled against a chemical database. In this mode the output of the analyzer provides the ability to perform material characterization, and even chemical identification at high ppm levels for a wide range of chemical species.

What is claimed is:

1. An optical spectral sensing device, for determining properties or composition of a gas sample, said device comprising:
    a measurement chamber configured to allow the gas sample to pass through the measurement chamber;
    a light source, wherein said light source is modulated to differentiate the light source from ambient thermal radiation;
    a detector system having a detector comprising multiple channels, wherein each channel corresponds to a different wavelength, the detector is configured for measuring the gas sample and generating a signal, wherein an output signal of the detector system is modulated and synchronized with modulation of the light source;
    a coupling apparatus for coupling the light source and the detector system to the measurement chamber; and
    electronics for providing energy for the light source and for receiving a signal generated by the detector in response to energy coupled to the detector by the coupling apparatus, the electronics providing direct output of properties of the gas sample.

2. The device of claim 1, further comprising a processor having a memory device in communication with the processor, wherein the memory stores gas sample data and calibration equations, wherein the processor is communicatively coupled to the detector system, wherein said processor is configured to calculate, based on the signal generated by the detector, a value of the concentration of at least one gas component of the gas sample.

3. The device of claim 1, wherein said detector system is configured to communicate with one or more digital signals from each channel to the processor, wherein each signal is evaluated relative to one or more reference signals and the concentration of the one or more gases present in the sample are calculated from one or more stored calibration equations for each species measured.

4. The device of claim 3, wherein said light source is modulated at a frequency between 10 Hz and 100 Hz.

5. The device of claim 1, wherein said detector is a pyroelectric detector configured to synchronize with the modulated light source.

6. The device of claim 1, wherein each detector channel is configured to filter a separate and distinct wavelength.

7. The device of claim 1, wherein the light source and detector system are juxtaposed across from one another, wherein the measurement chamber allows continuous flow through a pipe located between the light source and the detector system, wherein the light source is configured to pass across the flow path of the gas in the pipe.

8. The device of claim 1, wherein the electronics are integrated into the optical spectral sensing device.

9. An optical spectral sensing device, for determining properties of a gas sample, said device comprising:
    a measurement chamber configured to allow the gas sample to continuously pass through said chamber;
    a light source, wherein said light source is modulated to differentiate the light source from ambient thermal radiation;
    a detector system comprising a detector comprising multiple channels, wherein each channel corresponds to a different wavelength, wherein an output signal of the detector system is modulated and synchronized with modulation of the light source;

an extractor configured to draw the gas sample continuously through said measurement chamber;

a coupling apparatus for coupling the light source and the detector system to the measurement chamber; and electronics for providing energy for the light source and for receiving a signal generated by the detector in response to energy coupled to the detector system by the coupling apparatus, the electronics providing output of sample properties of the sample.

10. The device of claim 9, further comprising a processor having a memory device in communication with the processor for storing gas sample data, wherein said processor is communicatively coupled with at least one sensor, wherein said processor is configured to calculate, based on said detector system measurements, a value of the concentration of at least one gas component of a sample.

11. The device of claim 9, wherein said detector is configured to communicate one or more digital signals from each channel to the processor, wherein each signal is evaluated relative to one or more reference signals and the concentration of the one or more gases present in the sample are calculated from one or more stored calibration equations for each species measured.

12. The device of claim 9, wherein said light source is modulated at a frequency between 10 Hz and 100 Hz.

13. The device of claim 9, further comprising a processor having a memory device in communication with the processor for storing gas sample data, wherein said processor is communicatively coupled with at least one sensor, wherein said memory device includes one or more mode programs, wherein a first mode program is initiated by the processor to detect the presence of one or more pre-determined gases using the at least one sensor, wherein the gas is detected by using one or more statistical correlation algorithms and gas sample data to determine the presence of the pre-determined gas.

14. The device of claim 13, wherein said sensor is further configured to transmit a signal to a user to alert the presence of the pre-determined gas.

15. The device of claim 13, wherein said sensor further analyzes said pre-determined gas by initiating a second mode program to determine the concentration of said pre-determined gas, wherein said pre-determined gas concentration upon reaching a predetermined threshold, said sensor initiates an alert to a user indicating a potentially dangerous gas condition.

16. The device of claim 9, wherein the electronics are integrated into the optical spectral sensing device.

17. The device of claim 9, where each channel of said detector system is configured to monitor a specific chemical gas component to be further modeled against a chemical database stored on the memory.

18. A method for identifying the component gases and vapors of a sample, comprising:

supplying a detector system having a processor having a memory device in communication with the processor for storing gas sample data, wherein the detector system comprises a detector comprising multiple channels, wherein each channel corresponds to a different wavelength, wherein the detector is configured for measuring the sample and generating a signal;

selecting at least one specific wavelength to determine chemical functionality of a component;

supplying a light source to encode the light passing through the sample, wherein the light source is modulated to differentiate the light source from ambient thermal radiation;

synchronizing the detector system with the modulation of the light source;

detecting specific wavelength intensity of multi-wavelength radiation transmitted through the sample by a wavelength specific detector;

comparing detected wavelength intensities detected by the detector using correlation algorithms stored in the memory; and determining a presence of a component gas or vapor in the sample based at least in part on the detected intensities.

19. The method of claim 18, wherein presence of selected gases within a consumer home or workplace is detected.

20. The method of claim 18, wherein presence of hydrocarbon vapors is detected.

* * * * *